US011134168B2

(12) United States Patent
Koehl

(10) Patent No.: US 11,134,168 B2
(45) Date of Patent: *Sep. 28, 2021

(54) PRINTING FROM A HANDHELD DEVICE VIA A REMOTE SERVER

(71) Applicant: QUEST DIAGNOSTICS INVESTMENTS INC., Wilmington, DE (US)

(72) Inventor: John Koehl, Liberty Township, OH (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,376

(22) Filed: Jan. 27, 2020

(65) Prior Publication Data

US 2020/0162634 A1 May 21, 2020

Related U.S. Application Data

(63) Continuation of application No. 16/218,269, filed on Dec. 12, 2018, now Pat. No. 10,547,761, which is a
(Continued)

(51) Int. Cl.
*H04N 1/327* (2006.01)
*G06F 3/12* (2006.01)
(Continued)

(52) U.S. Cl.
CPC ....... *H04N 1/32776* (2013.01); *G06F 3/1292* (2013.01); *G06K 9/00456* (2013.01);
(Continued)

(58) Field of Classification Search
CPC ........ G16H 70/20; G16H 70/40; G16H 20/10; G16H 40/67; G16H 30/40; H04N 1/2361;
(Continued)

(56) References Cited

U.S. PATENT DOCUMENTS 8,508,757 B1 8/2013 Koehl
8,860,972 B2 10/2014 Koehl
(Continued)

*Primary Examiner* — Juan M Guillermety
(74) *Attorney, Agent, or Firm* — Jon E. Gordon; Haug Partners LLP

(57) ABSTRACT

Systems and methods are provided though which a transaction, e.g., in a multi-tier, distributed application may be initiated from a portable or hand-held device, such as a smartphone. A computer system or systems, possibly remote from the device, may approve the transaction, complete it, or both, and the remote computer system or systems may cause a document to be printed, e.g., by a printer physically proximate to the device.

Aspects of the invention are illustrated by embodiments in which a drug prescription may be created electronically using a hand-held device. In such an embodiment, the prescription may be transmitted to one or more remote computer systems, such as an application server, for processing. If specified, the remote computer systems may cause a prescription to be printed, e.g., at a printer near the prescriber's location. The prescriber may sign the printed prescription and give it to a patient or pharmacy.

24 Claims, 16 Drawing Sheets

Related U.S. Application Data continuation of application No. 15/838,671, filed on Dec. 12, 2017, now Pat. No. 10,194,049, which is a continuation of application No. 15/483,657, filed on Apr. 10, 2017, now Pat. No. 9,973,650, which is a continuation of application No. 14/514,116, filed on Oct. 14, 2014, now Pat. No. 9,619,622, which is a continuation of application No. 13/950,878, filed on Jul. 25, 2013, now Pat. No. 8,860,972, which is a continuation of application No. 12/845,931, filed on Jul. 29, 2010, now Pat. No. 8,508,757, which is a continuation of application No. 12/646,144, filed on Dec. 23, 2009, now abandoned.

(51) Int. Cl.
| | | |
|---|---|---|
| *H04N 1/00* | (2006.01) | |
| *G16H 70/20* | (2018.01) | |
| *G16H 40/67* | (2018.01) | |
| *G16H 70/40* | (2018.01) | |
| *G06K 9/00* | (2006.01) | |
| *H04N 1/23* | (2006.01) | |
| *G16H 20/10* | (2018.01) | |
| *G16H 30/40* | (2018.01) | |

(52) U.S. Cl.
CPC .............. *G16H 20/10* (2018.01); *G16H 30/40* (2018.01); *G16H 40/67* (2018.01); *G16H 70/20* (2018.01); *G16H 70/40* (2018.01); *H04N 1/00307* (2013.01); *H04N 1/00344* (2013.01); *H04N 1/2361* (2013.01); *H04N 2201/0046* (2013.01); *H04N 2201/0055* (2013.01); *H04N 2201/3253* (2013.01)

(58) Field of Classification Search
CPC ... H04N 2201/0046; H04N 2201/3253; H04N 1/32776; H04N 2201/0055; H04N 1/00307; H04N 1/00344; G06K 9/00456; G06F 19/3456; G06F 3/1292
USPC ........................................................ 358/1.15
See application file for complete search history.

(56) References Cited

U.S. PATENT DOCUMENTS

| | | | |
|---|---|---|---|
| 9,019,535 | B1 | 4/2015 | Hansen |
| 10,194,049 | B2 | 1/2019 | Koehl |
| 10,547,761 | B2* | 1/2020 | Koehl ................ H04N 1/00307 |
| 2002/0035484 | A1* | 3/2002 | Mccormick ............ G16H 20/10 |
| | | | 705/2 |
| 2006/0044598 | A1 | 3/2006 | Etelapera |
| 2007/0136376 | A1 | 6/2007 | Kusakabe |
| 2010/0063836 | A1 | 3/2010 | Ballard |
| 2010/0309510 | A1 | 12/2010 | Hansen |

* cited by examiner

928 — LIPID PANEL WITH REFLEX TO DIREC...
Status Final    Reported 12/5/08 1:54 AM Patient: Smith, Thomas
Lab Detail See the full report for additional information 920 — @*TRIGLYCERIDES*        278 H    <150 mg/dl 920 — @*CHOLESTEROL, TOTAL*   284 H    125-200 mg/dl 920 — HDL CHOLESTEROL         67 H    >OR=40mg...

920 — @*LDL-CHOLESTEROL*      161 H    <130 mg/dl (c...

920 — CHOL/HDL RATIO          4.2    <OR=5.0 (ca...

Full Report — 924

FIG. 15
950

```
.ııll    3G         9:50 PM              🔋
┌──────┐  Smith, Thomas          ┌───────┐
│ Done │  Lab Report             │ Print │─── 964
└──────┘                         └───────┘
```

SAMPLE REPORT

Patient Information          REPORT STATUS Partial

Quest Diagnostics Incorporated      Age: 45        Ordering Physician
                                    Gender: M SPECIMEN INFORMATION
LAB REF NO:
                                                   Client Information
COLLECTED:  03/30/2004    11:00
RECEIVED:   03/30/2004    13:48
REPORTED:   03/31/2004    17:33

| Test Name | In Range | Out of Range | Reference Range | Lab |
|---|---|---|---|---|
| LIPID PANEL | | | | |
| TRIGLYCERIDES | | 172 H | <150 MG/DL | IG |
| CHOLESTEROL, TOTAL | | 216 H | <200 MG/DL | IG |
| HDL CHOLESTEROL | 42 | | > or = 40 MG/DL | IG |
| LDL-CHOLESTEROL | | 140 H | <130 MG/DL (CALC) | IG |
| CHOL/HDLC RATIO | | 5.1 H | <5.0 (CALC) | IG |

UPPER RESPIRATORY ALLERGY PROFILE REGION X

ALTERNARIA ALTERNATA
  (M6) IGE        Pending

BERMUDA GRASS
  (G2) IGE        Pending                        960

CLADOSPORIUM
  HERBARUM (M2)IGE  Pending

COCKROACH (I6) IGE  Pending

COMMON RAGWEED
  (SHORT) (W1) IGE  Pending

PRINTING FROM A HANDHELD DEVICE VIA A REMOTE SERVER

CROSS REFERENCE TO RELATED APPLICATION

This application is a continuation of U.S. patent application Ser. No. 16/218,269, filed 12 Dec. 2018 and titled "Printing from a Handheld Device via a Remote Server"; which is a continuation of U.S. patent application Ser. No. 15/838,671, filed 12 Dec. 2017 and titled "Printing from a Handheld Device via a Remote Server"; which is a continuation of U.S. patent application Ser. No. 15/483,657, now U.S. Pat. No. 9,973,650, filed 10 Apr. 2017 and titled "Printing from a Handheld Device via a Remote Server"; which is a continuation of U.S. patent application Ser. No. 14/514,116, now U.S. Pat. No. 9,619,622, filed 14 Oct. 2014 and titled "Printing from a Handheld Device via a Remote Server"; which is a continuation of U.S. patent application Ser. No. 13/950,878, now U.S. Pat. No. 8,860,972, filed 25 Jul. 2013 and titled "Printing from a Handheld Device via a Remote Server"; which is a continuation of U.S. patent application Ser. No. 12/845,931, now U.S. Pat. No. 8,508,757, filed 29 Jul. 2010 and titled "Printing from a Handheld Device via a Remote Server"; which is a continuation of U.S. patent application Ser. No. 14/646,144, now abandoned; which was filed on 23 Dec. 2009 and titled "Printing from a Handheld Device via a Remote Server", all of which are incorporated herein by reference.

This application contains material relating to medical services and medical information. The provision and handling of some medical services and medical information are regulated, as for example, by the United States Government, the various state governments, and other governmental agencies within the United States and elsewhere. The disclosure herein is made solely in terms of logical and financial possibility and advantage, without regard to possible statutory, regulatory, or other legal considerations. Nothing herein is intended as a statement or representation of any kind that any method or process proposed or discussed herein does or does not comply with any statute, law, regulation, or other legal requirement whatsoever, in any jurisdiction; nor should it be taken or construed as doing so.

BACKGROUND

Handheld electronic devices may process, store, and retrieve data, which they may share using voice and/or data networks. They may therefore serve as platforms upon which applications may be created for various purposes. Mobile telephones that include such capability, or "smartphones," have enjoyed great popularity.

Handheld devices may nonetheless be limited in ways that other data processing devices, including, for example, portable computers, are not. One such limitation is that such devices may provide, at best, limited support for printing and may often provide no support for printing at all. Such limits may reflect factors that may include, for example, the relatively limited storage and processing capabilities of handheld devices and the difficulty of associating a printer with a device that may be carried and used nearly anywhere and any time, among many others.

BRIEF SUMMARY OF THE INVENTION

Embodiments of the invention provide systems and methods for initiating a transaction, which may include printing of a document, from a handheld device. In an embodiment of the invention, a user of a device may initiate printing of a document, e.g., from within an application on the device. The application may cause the device to transmit information, e.g., in the form of one or more queries, to a server, which may be physically remote from the device, the printer that will be used, or both.

The server may process and/or store some or all of the transmitted information, which may include processing that is not directly related to the printing operation. The server may identify a printer that is to service the printing request, and in an embodiment of the invention, the server may use information about the physical and/or logical location of the device to select the printer. The server may then transmit information to the printer and/or a server associated with the printer to cause the printer to service the print request.

Embodiments of the invention may relate to the electronic prescribing, e.g., of medication, by a health care professional, such as a physician. (For the sake of convenience, a person creating a prescription in connection with an embodiment of the invention may be referred to simply as a "physician," but it will be appreciated that depending, e.g., on the jurisdiction, a drug may be prescribed by a health care provider other than a physician. Unless otherwise required by the context, a reference to a physician in connection with an embodiment of the invention may include such other provider.)

Electronic prescribing may provide several advantages, including, for example, automatic checking for drug interactions and/or insurance coverage, automatic updating of a patient's chart and/or other records, and making drug information readily available at the time of prescription, among others. An electronic prescribing application according to an embodiment of the invention may be created for a handheld device, e.g., such as referred to above. In an embodiment of the invention, a physician may create a prescription electronically, which may then be transmitted, e.g., to a server, which may then transmit information to a printer to cause a paper prescription to be printed. The paper prescription may then be signed by the physician.

In an embodiment of the invention, medical information (which may include information about payment and/or insurance or other coverage for medical products and/or services) may be available to a user of a handheld device through an application. The application may similarly support printing of such information via a server. In an embodiment of the invention, the selection of the destination printer may vary depending, e.g., on the type of information to be printed.

In an embodiment of the invention, a method is provided of printing a document, in response to a request from a handheld device, in connection with a computer system that comprises one or more processors, one or more interfaces operatively coupled to at least one of the processors, and one or more databases operatively coupled to at least one of the processors. The method comprises receiving from the handheld device, through one or more of the interfaces, one or more queries comprising information related to a transaction; approving the transaction based on the information comprised by the queries; selecting a printing system based on the information comprised by the queries; and transmitting to the selected printing system, though one of the interfaces, information sufficient to cause the printing system to print a document that is related to the transaction.

In an embodiment of the invention, at least one of the queries comprises location information specifying the location of the handheld device, and selecting a printing system comprises selecting a printing system based on the location information. In embodiments of the invention, the printing system, the handheld device, or both of them are physically located remotely from the physical location of the computer system.

In an embodiment of the invention, the transaction is a prescription for a drug. In one such embodiment, the drug is a controlled substance; and the document is a written prescription for the drug in a form for signature by a prescriber.

In an embodiment of the invention, the method comprises generating a representation of the document in a page description language, wherein the transmitted information comprises the generated representation of the document.

Embodiments of the invention include computer systems configured to carry out the above methods and computer-readable media encoded with instructions that, when executed by one or more processors within a computer system, cause the computer system to carry out those methods.

BRIEF DESCRIPTION OF THE DRAWINGS

FIG. 14 depicts a lab detail screen according to an embodiment of the invention.

FIG. 15 depicts a page of a full laboratory result as may be presented in an embodiment of the invention.

DETAILED DESCRIPTION OF PREFERRED EMBODIMENTS

A description herein of one or more embodiments of the invention may refer to a handheld device. The term "handheld device" may be used herein to refer to any such device, which may be, e.g., easily portable, powered from an internal source, intended for use while the user supports the device in one or both hands, and capable of sending and receiving information, e.g., wirelessly via one or more voice and/or data networks. For brevity, an application (such as, e.g., a software application) for use on a handheld device may be referred to herein as a "handheld application."

It will be appreciated that an application, operating on the handheld device to process information, may use one or more facilities provided by the hardware and/or software of a handheld device to cause information to be transmitted from the handheld device. Similarly, information may be received by the handheld device and, e.g., made available to an application by one or more facilities provided by the hardware and/or software of the handheld device. For brevity, such operations may be referred to simply as transmission and reception of information, respectively, by the application.

Figure 1:
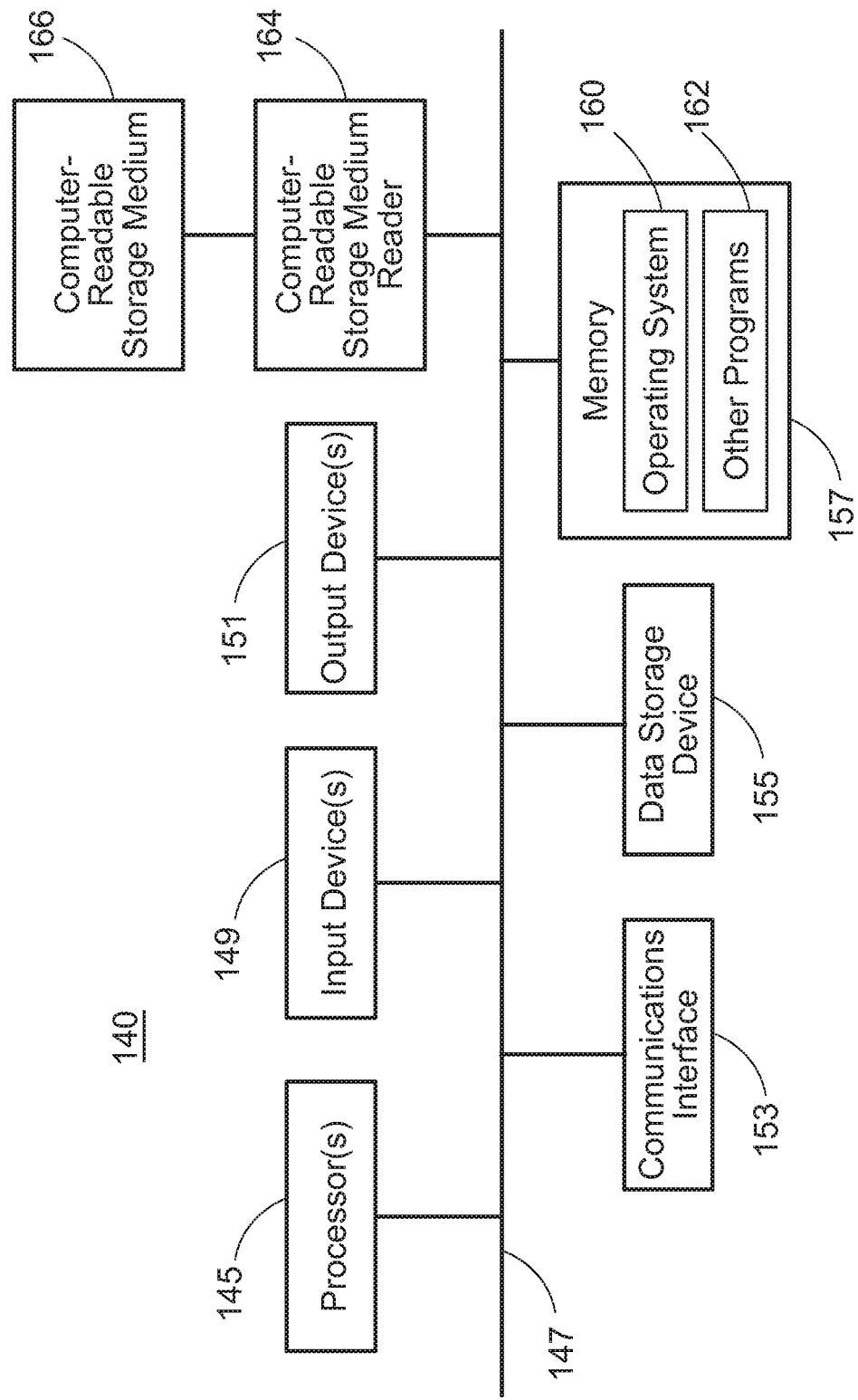
FIG. 1 depicts functional components of a representative computer system.

Embodiments of the invention may be practiced in connection with one or more programmable digital computers. FIG. 1 is a block diagram of a representative computer system 140 such as may be used in connection with an embodiment of the invention.

The computer system 140 includes at least one processor 145, such as, e.g., an Intel Core™ 2 microprocessor or a Freescale™ PowerPC™ microprocessor, coupled to a communications channel 147. The computer system 140 further includes at least one input device 149 such as, e.g., a keyboard, mouse, touch pad or screen, or other selection, pointing, and/or input device, at least one output device 151 such as, e.g., a CRT or LCD display, a communications interface 153, a data storage device 155, which may comprise, e.g., a magnetic disk, an optical disk, and/or another computer-readable storage medium, and memory 157 such as Random-Access Memory (RAM), each coupled to the communications channel or bus 147. The communications interface 153 may be coupled to a network such as the Internet.

A person skilled in the art will recognize that a computer system may have multiple channels 147, which may be interconnected. In a configuration comprising multiple interconnected channels, components may be considered to be coupled to one another despite being directly connected to different communications channels. Additionally, any connection between or among any one or more components may include one or more interfaces.

One skilled in the art will recognize that, although the data storage device 155 and memory 157 are depicted as different units, the data storage device 155 and memory 157 can be parts of the same unit or units, and that the functions of one can be shared in whole or in part by the other, e.g., as RAM disks, virtual memory, etc. It will also be appreciated that any particular computer may have multiple components of a given type, e.g., processors 145, input devices 149, communications interfaces 153, etc.

The data storage device 155 and/or memory 157 may store instructions executable by one or more processors 145 or kinds of processors, data, or both, which may represent, e.g., one or more operating systems, programs, and/or other functions and/or data.

Figure 2:
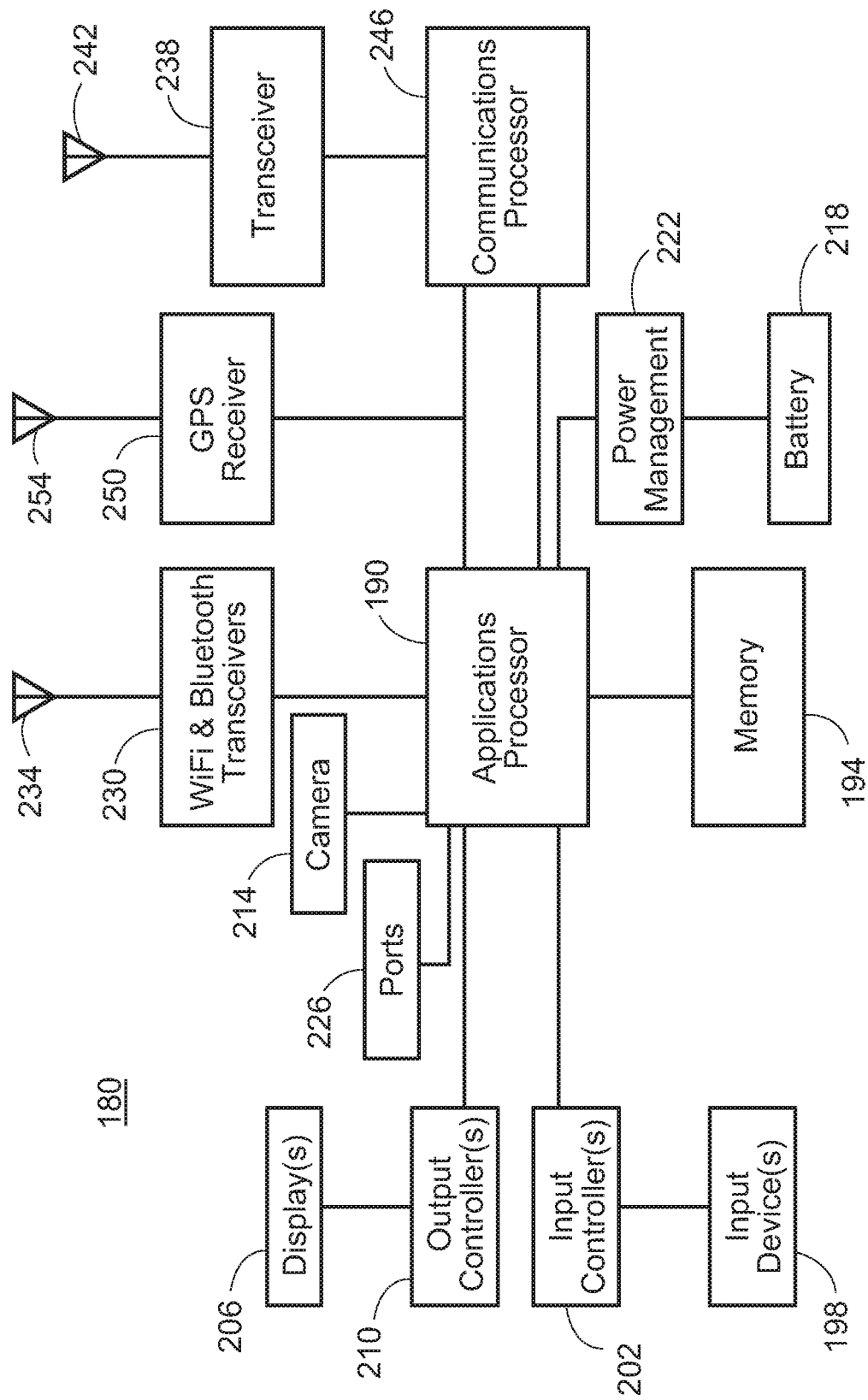
FIG. 2 depicts functional components of a representative handheld device.

FIG. 2 is a simplified block diagram that illustrates functional components that may be found in a handheld device 180, in connection with an embodiment of the invention. Functions in a handheld device may be controlled, e.g., by a programmable applications processor or microcontroller 190. Memory 194 coupled to the applications processor 190 may include one or more kinds of persistent and/or volatile memory and may store, e.g., instructions to be executed by the applications processor 190 and/or data upon which the applications processor 190 may operate, which may represent, e.g., one or more operating systems, programs, and/or other functions and/or data, among other things.

One or more input devices 198 may be coupled to the applications processor 190, e.g., directly and/or via one or more input controllers 202. Examples of input devices 198 may include, among other possibilities, one or more buttons and/or switches (which may include buttons or switches configured as one or more keypads and/or keyboards), touchscreens, proximity sensors, accelerometers, and/or photosensors.

One or more output devices, including, e.g., one or more displays 206, may be coupled to the applications processor 190, e.g., directly and/or via one or more output controllers 210. A handheld device 180 may output information in ways that do not involve a display 206, e.g., by controlling illumination of one or more LEDs or other devices.

In a handheld device 180, which may be, e.g., a device capable of acting as a telephone, the input devices 198 and output devices 206 may include devices configured to detect and/or emit sound (not pictured).

A handheld device 180 may comprise a camera 214 capable of recording, e.g., still and/or moving pictures. As depicted, the camera 214 may be coupled to the applications processor 190.

The handheld device 180 may be powered, e.g., by one or more batteries 218. The applications processor 190 and/or other components may be powered, e.g., via a power management unit 222 coupled to the battery 218. If the battery 218 is rechargeable, the power management unit 222 may monitor and/or control charging and/or discharging of the battery 218. Power to charge the battery 218 may be supplied, e.g., via one or more external ports 226.

A handheld device 180 may include one or more external ports 226 that may support analog and/or digital input and/or output.

A handheld device 180 may be configured to participate in one or more local area networks (LANs). For example, as FIG. 2 depicts, a handheld device 180 may include one or more transceivers 230 supporting, e.g., Bluetooth® and/or Wi-Fi™ networking. Such a transceiver 230 may be connected, e.g., to one or more antennas 234 and, as FIG. 2 depicts, may be coupled to the applications processor 190.

A handheld device 180 may be configured to interact with one or more wide-area networks (WANs), such as, e.g., cellular voice and/or data networks. For example, as FIG. 2 depicts, a handheld device may comprise one or more cellular transceivers 238 and associated antennas 242. A transceiver 238, as in the depicted device 180, may be coupled to a device such as a communications processor 246, which may include functions such as, for example, of a digital signal processor and/or a microcontroller. A communications processor 246 in a handheld device 180 may also be coupled directly or indirectly to the applications processor 190.

A handheld device 180 may include a unit 250 that is capable of receiving and/or interpreting signals from the Global Positioning System (GPS). The GPS receiver 250 may be coupled to its own antenna 254. The GPS receiver may also be coupled in a handheld device 180 to the applications processor 190, the communications processor 246, or both.

It will be appreciated that FIG. 2 and the discussion of it herein are not meant to describe precisely any particular device, but rather to illustrate functions that may commonly be found in certain classes of devices. A handheld device suitable for use in connection with an embodiment of the invention may differ in its physical or logical organization from the depicted device, and such a device may comprise one or more other components in addition to, or instead of, any one or more discussed or depicted components.

Figure 3:
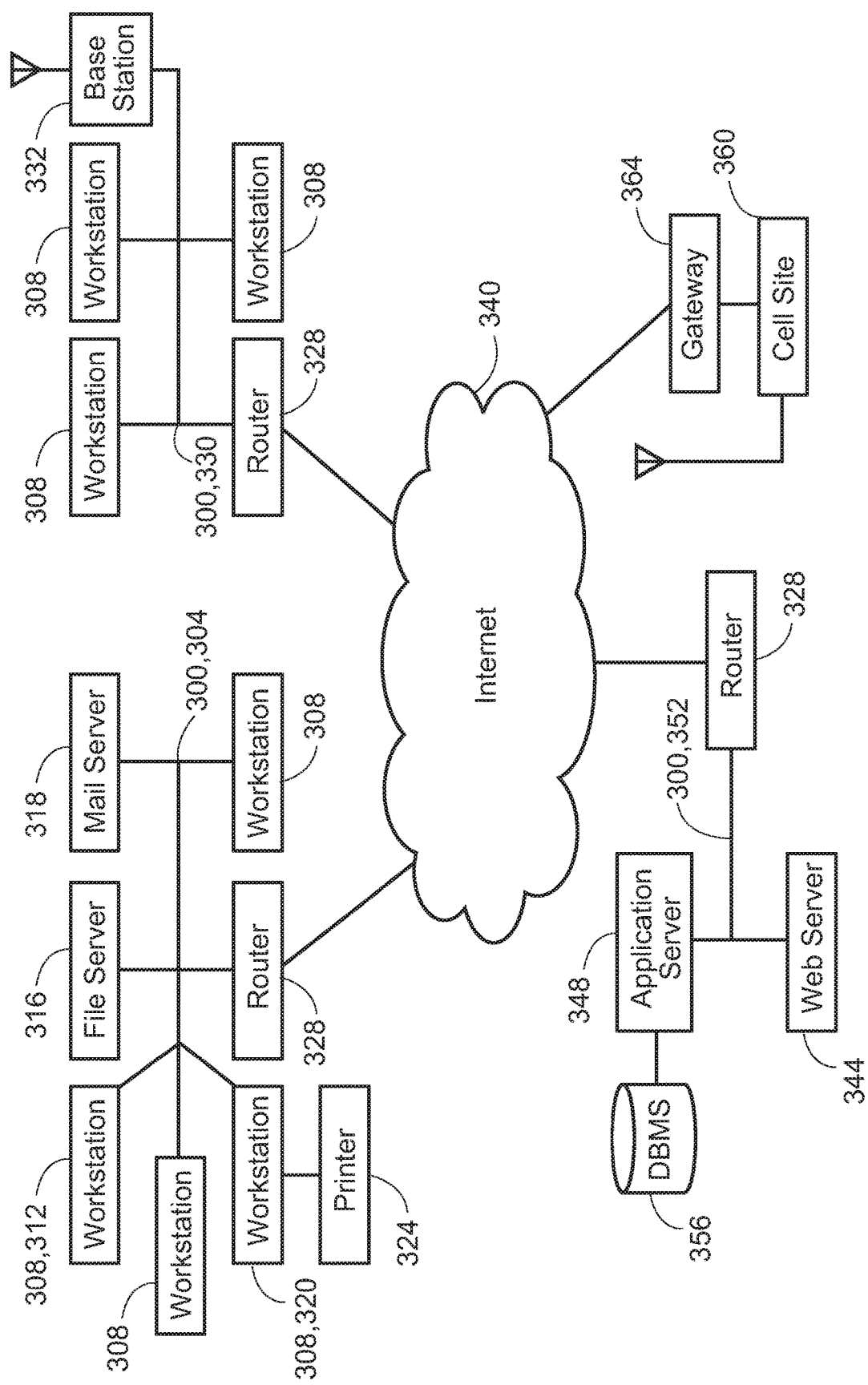
FIG. 3 depicts elements of interconnected wired and wireless networks.

FIG. 3 depicts elements of wired and wireless networks 300 such as, e.g., one or more computers, handheld devices, or both, may use to communicate in connection with an embodiment of the invention. A network 304 may, for example, connect one or more workstations 308 with each other and with other computer systems, such as file servers 316 or mail servers 318. The connection may be achieved tangibly, e.g., via optical cables, or wirelessly.

A network 300 may enable a computer system to provide services to other computer systems, consume services provided by other computer systems, or both. For example, a file server 316 may provide common storage of files for one or more of the workstations 308 on a network 304. A workstation 312 may send data including a request for a file to the file server 316 via the network 304 and the file server 316 may respond by sending the data from the file back to the requesting workstation 312.

The terms "workstation," "client," and "server" may be used herein to describe a computer's function in a particular context, but any particular workstation may be indistinguishable in its hardware, configuration, operating system, and/or other software from a client, server, or both. Further, a computer system may simultaneously act as a workstation, a server, and/or a client. For example, as depicted in FIG. 3, a workstation 320 is connected to a printer 324. That workstation 320 may allow users of other workstations on the network 304 to use the printer 324, thereby acting as a print server. At the same time, however, a user may be working at the workstation 320 on a document that is stored on the file server 316.

The terms "client" and "server" may describe programs and running processes instead of or in addition to computer systems such as described above. Generally, a (software) client may consume information and/or computational services provided by a (software) server.

The term "printing system" may be used in a broad sense herein to refer to, e.g., a printer, or a print server and one or more associated printers, configured such that a computer system may send documents and/or commands to the printing system, which may in response print one or more documents or cause one or more documents to be printed by one or more of the printers that the printing system comprises. For example, referring to FIG. 3, "printing system" may refer to the printer 324 or to the combination of the workstation 320 (insofar as it operates as a print server) and the printer 324.

A network 304 may be connected to one or more other networks 300, e.g., via a router 328. A router 328 may also act as a firewall, monitoring and/or restricting the flow of data to and/or from a network 300 as configured to protect the network. A firewall may alternatively be a separate device (not pictured) from the router 328.

Connections within and between one or more networks may be wired or wireless. For example, a computer or handheld device may participate in a LAN using one or more of the standards denoted by the term Wi-Fi™ or other technology. Wireless connections to a network 330 may be achieved through use of, e.g., a device 332 that may be referred to as a "base station", "gateway", or "bridge", among other terms.

A network of networks 300 may be referred to as an internet. The term "the Internet" 340 refers to the worldwide network of interconnected, packet-switched data networks that uses the Internet Protocol (IP) to route and transfer data. A client and server on different networks may communicate via the Internet 340. For example, a workstation 312 may request a World Wide Web document from a Web Server 344. The Web Server 344 may process the request and pass it to, e.g., an Application Server 348. The Application Server 348 may then conduct further processing, which may include, for example, sending data to and/or receiving data from one or more other data sources. Such a data source may include, e.g., other servers on the same network 352 or a different one and/or a Database Management System ("DBMS") 356.

Depending on the configuration, a computer system such as the application server 348 in FIG. 3 or one or more of its processors may be considered to be coupled, e.g., to the DBMS 356. In addition to or instead of one or more external databases and/or DBMSs, a computer system may incorporate one or more databases, which may also be considered to be coupled to one or more of the processors within the computer system.

Devices, including, e.g., suitably configured handheld devices and computers, may communicate with Internet-connected hosts. In such a connection, the device may communicate wirelessly, e.g., with a cell site 360 or other base station. The base station may then route data communication to and from the Internet 340, e.g., directly or indirectly through one or more gateways 364 and/or proxies (not pictured).

A handheld device may be capable of storing and/or executing one or more application programs (or "applications"). In an embodiment of the invention, an application may provide, e.g., information about one or more patients to a user, who may be a health-care professional such as a physician. Such an application may further assist the user in providing health care, e.g., by allowing the user to add or modify information, send messages, and/or order laboratory tests, among other functions.

Figure 4:
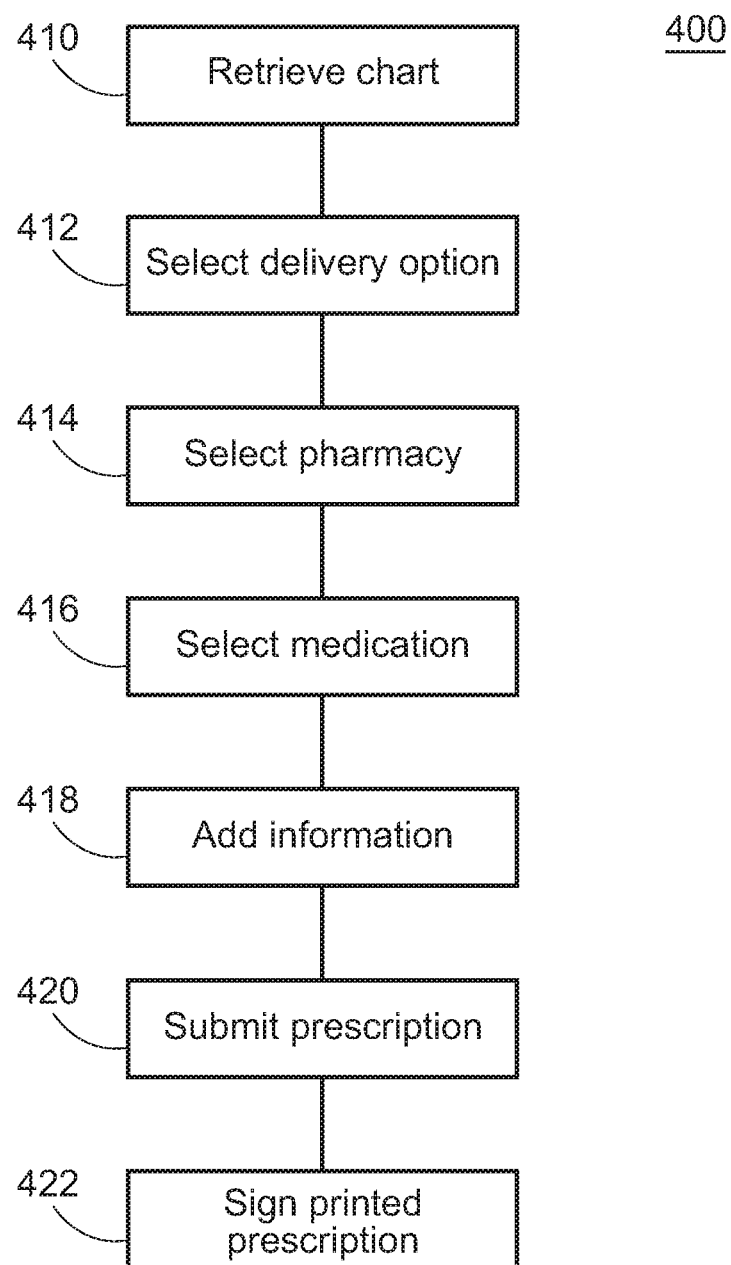
FIG. 4 depicts creation of a prescription according to an embodiment of the invention.

An application may also allow a user to prescribe medication electronically. FIG. 4 depicts a workflow 400 for creating a prescription according to an embodiment of the invention. In block 410, the prescriber may enter the workflow by accessing a summary of the patient's chart. Precisely how to access a particular patient's summary may vary depending on the application.

Figure 5:
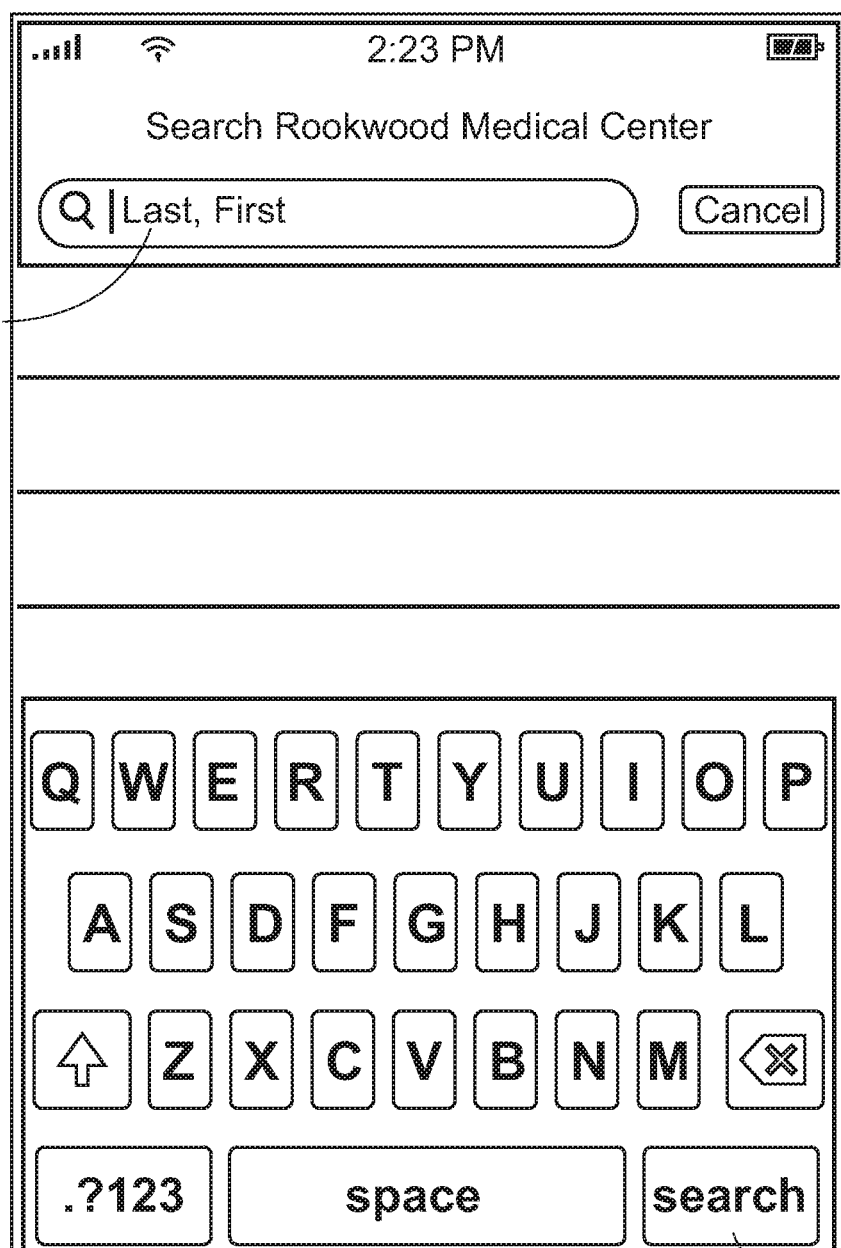
FIG. 5 depicts a search screen that may be presented by an application on a handheld device in connection with an embodiment of the invention.
Figure 6:
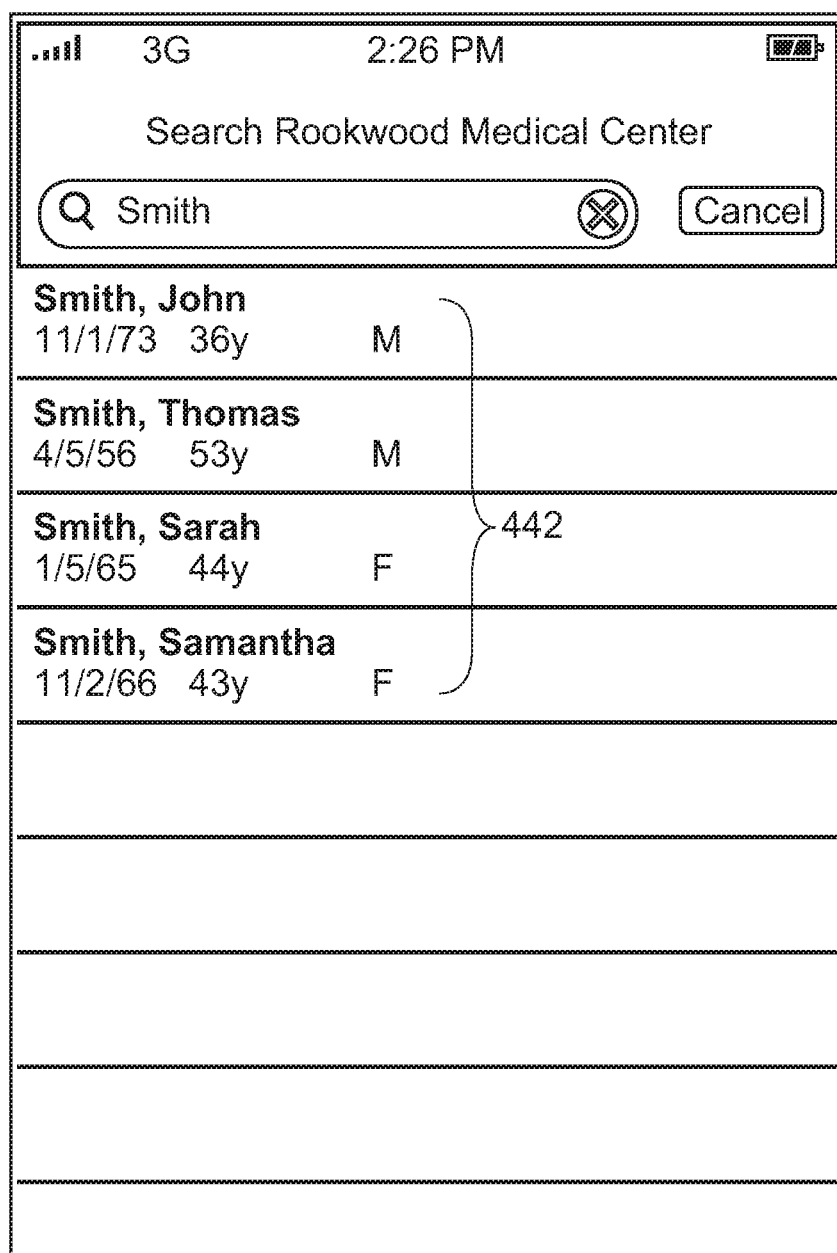
FIG. 6 depicts a patient search results screen that may be presented by an application on a handheld device in connection with an embodiment of the invention.

In an embodiment of the invention, a user may have one or more ways to recall a patient's summary. One such way, for example, may be to search for a patient by name. In one application, in connection with an embodiment of the invention, a search display 430, e.g., as in FIG. 5, may include a text entry field 434. The user may enter all or part of a patient's name in the text entry field 434 and then initiate the search, e.g., by selecting a control 438 labeled "Go" or "Search". A list of matching patients' names 442 may then appear, e.g., as in a display 450 such as FIG. 6 depicts, and the user may select the intended patient from the list 442.

Other ways for a user to recall a patient's summary in an embodiment of the invention may include, among others, selecting an icon or other control (not pictured) while viewing information related to the patient, e.g., a notification or alert related to the patient or a result for a lab test related to the patient. An application may, in connection with an embodiment of the invention, maintain a list, e.g., of frequently-accessed or "favorite" patients, and the user may select a patient from such a list (not pictured).

Figure 7:
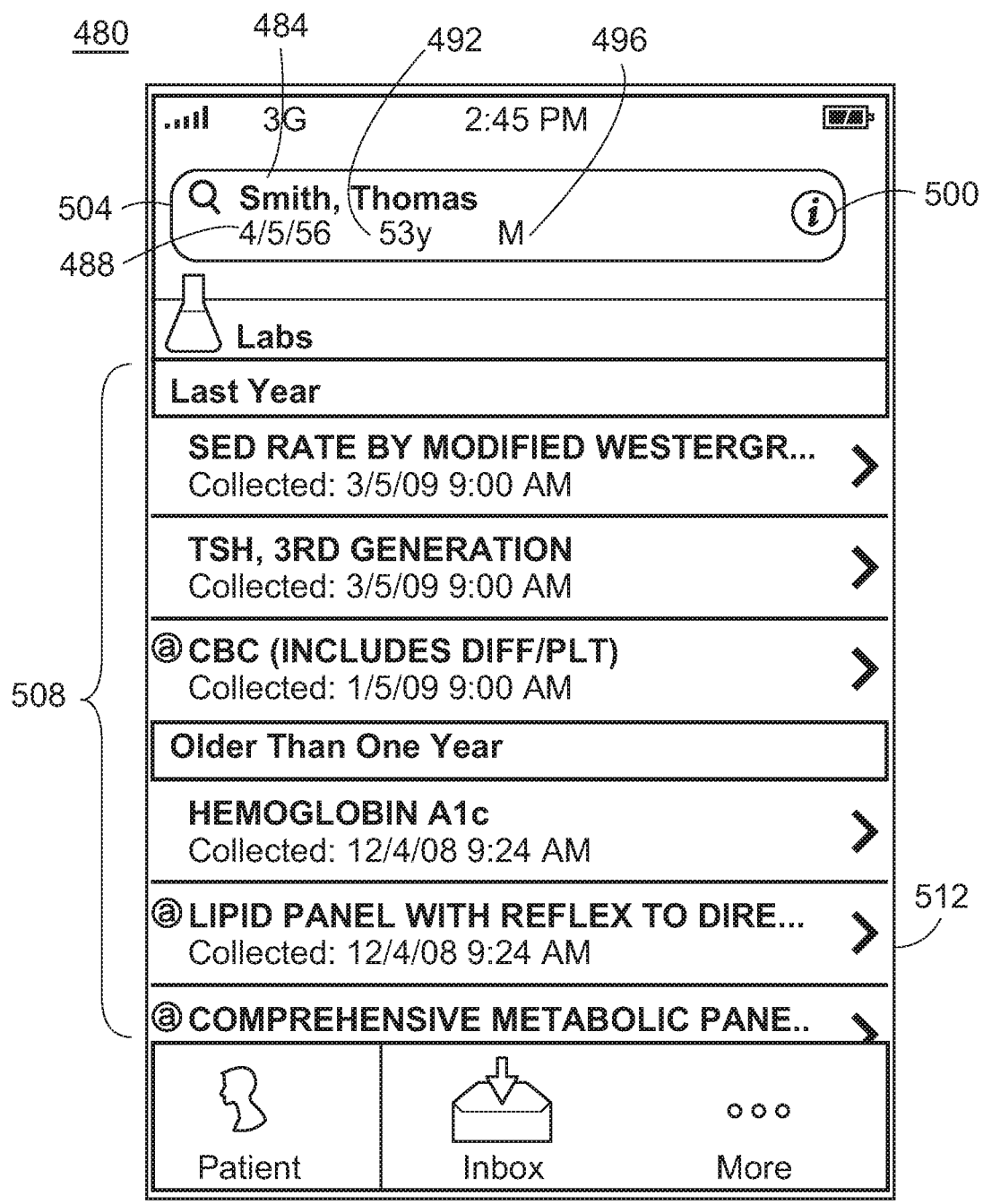
FIG. 7 depicts a patient summary screen that may be presented by an application on a handheld device in connection with an embodiment of the invention.

In response to the user's selection, summary information for the patient may appear. FIG. 7 depicts a display 480 of summary information for a fictitious patient according to an embodiment of the invention. As depicted, the summary information may include, for example, the patient's name 484, date of birth 488, age 492, and sex 496. Selection of an information button 500, may cause display (not pictured) of the patient's demographic information, such as, e.g., address, telephone number, chart identifier, etc.

A search icon 504 may be provided, which may allow the user to search for another patient.

In the depicted application, the patient's chart, when first displayed, may list laboratory results 508 for the patient, but other information and/or functions may be available. For example, in an embodiment such as FIG. 7 depicts, a gesture may move the display left or right and replace it with a display (not pictured), e.g., of allergies, active medications, notes, and/or other information.

Figure 8:
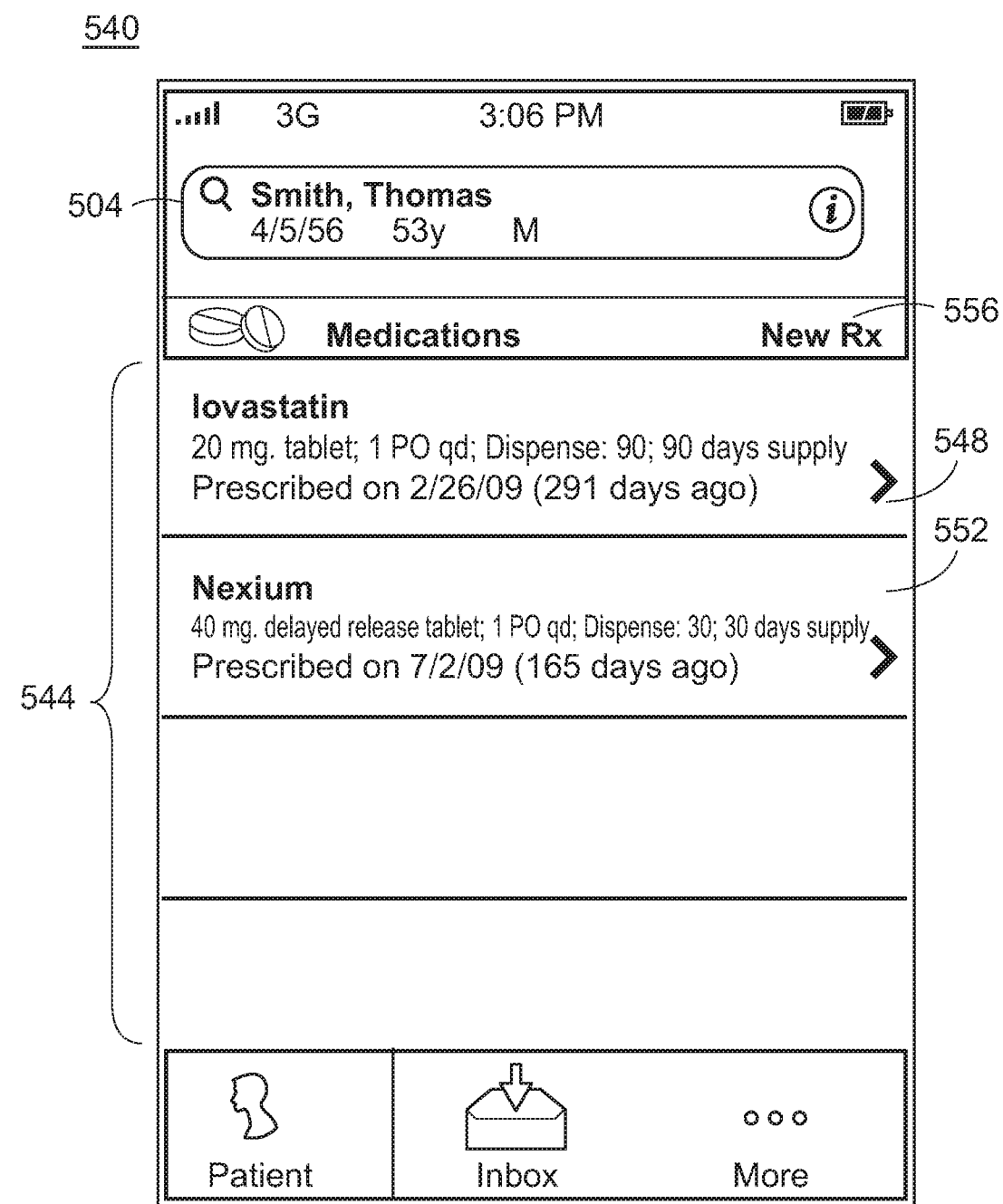
FIG. 8 depicts a patient's active medication screen that may be presented by an application on a handheld device in connection with an embodiment of the invention.

In an embodiment of the invention, a user may write a prescription from the patient's active medication screen 540, e.g., as FIG. 8 depicts. As depicted, the screen 540 displays a list 544 of recently-prescribed medications 548, 552 for the patient. To write a new prescription from this screen 540, the user may then select "New Rx" 556.

Figure 9A:
FIGS. 9a and 9b depicts parts of a prescription screen that may be presented by an application on a handheld device in connection with an embodiment of the invention.
Figure 9B:
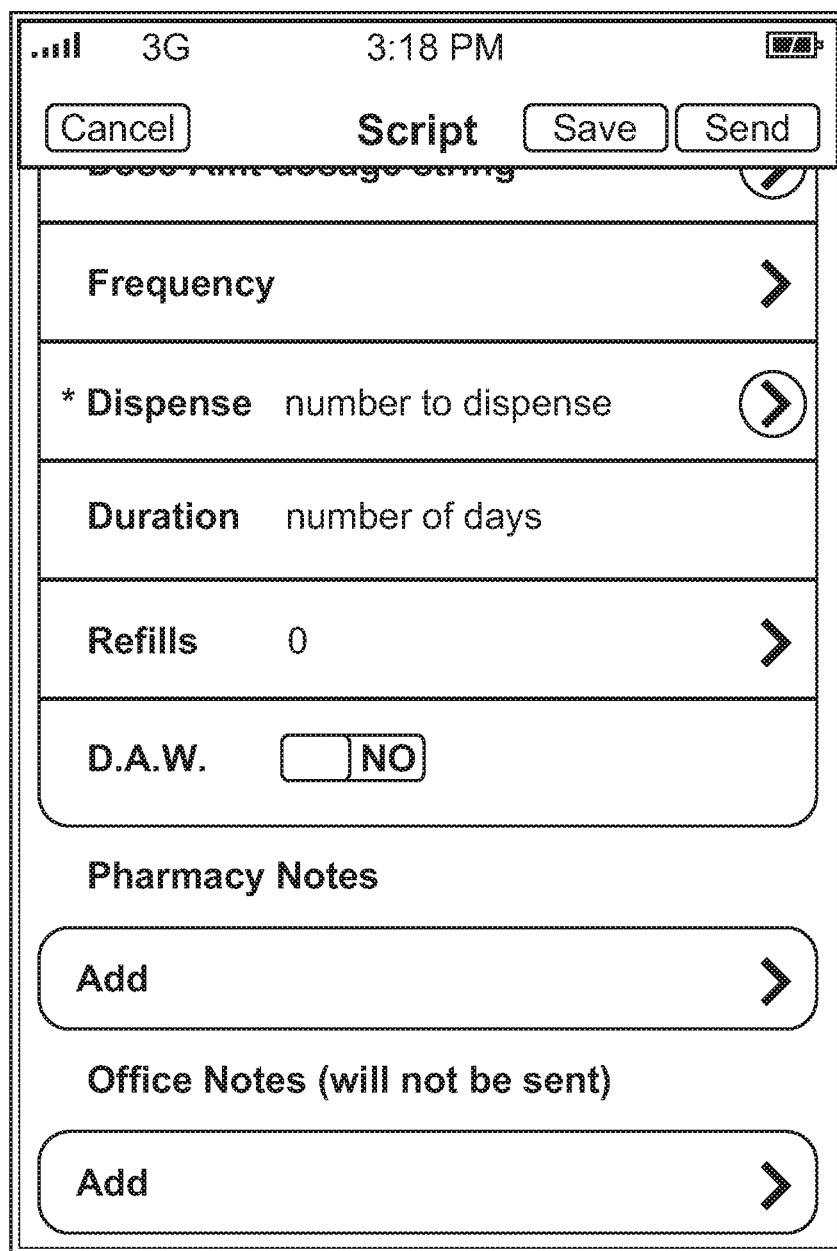

In response to the selection of "New Rx" 556, a prescription screen 580 may be displayed, e.g., as in FIGS. 9a and 9b. From the prescription screen 580, the user may create the prescription, e.g., by selecting or otherwise specifying attributes of the prescription in blocks 412, 414, 416, and 418 of FIG. 4. The prescription screen 580 of FIGS. 9a and 9b may, for example, allow the user to select a delivery option, a pharmacy 590, and a medication 594.

In block 412 of FIG. 4, according to an embodiment of the invention, the user may select a delivery option, which may include selecting a pharmacy to which the prescription may be sent electronically. In the depicted embodiment, the user may specify the delivery method by selecting the currently-selected pharmacy 590 from the screen 580 in FIG. 9a. As a result, the user may be presented with a pharmacy selection screen 620, e.g., as FIG. 10 depicts.

Figure 10:
FIG. 10 depicts a delivery method and selection screen that may be presented by an application on a handheld device in connection with an embodiment of the invention.

In an embodiment of the invention such as FIG. 10 depicts, the user is presented with delivery options that include "Sample" 630, "Mail Order" 634, and "Auto-Print" 638.

In an embodiment of the invention, the "Sample" 630 delivery option may mean, e.g., that a prescription record may be, e.g., created and stored with the patient's chart, but that no electronic prescription will be created. One use for this delivery option may occur when a physician dispenses a sample of the prescribed medication directly to the patient. Also, the "Sample" 630 delivery option may be chosen if a prescription is delivered, e.g., as a handwritten prescription on a blank prescription form.

Reflecting these applications of the "Sample" 630 delivery option, in an embodiment of the invention, if the "Sample" 630 delivery option is selected, the "Send" button 606 (FIG. 9a) may be disabled, leaving the "Save" button 602 (FIG. 9a) as the only active control allowing the user to process the prescription.

The "Mail Order" delivery option 634 may in an embodiment of the invention indicate that the prescription will be submitted electronically or faxed to a mail order fulfillment center that processes and mails the medication(s) to the patient's home address. A patient's chart may indicate the mail order fulfillment center that is associated with the patient directly or indirectly, e.g., by identifying a mail-order pharmacy associated with a pharmacy benefits manager ("PBM") that may administer a prescription plan in which the patient participates. If a patient's chart indicates that the patient is associated with more that one mail order fulfillment center, the user in an embodiment of the invention may select which center is to receive the prescription. A record for a mail order fulfillment center may be associated with information specifying how an electronic or facsimile prescription may be delivered to that fulfillment center.

The "Auto-Print" 638 delivery option in an embodiment of the invention may allow a user to enter a prescription, e.g., electronically using an application on the handheld device, but have a paper prescription printed automatically, which the prescriber may then sign and deliver to the patient. In an embodiment of the invention, as discussed below, one or more printers may be associated, e.g., with respective locations. When the "Auto-Print" 638 delivery option is selected, the user's current location may be used to set a default choice of printer for the prescription. In an embodiment of the invention, the user may be able to override the default assignment of a printer, e.g., by selecting a particular printer from a list (not pictured).

To choose a pharmacy as a delivery option, the user may in an embodiment of the invention select a pharmacy from a list presented in the pharmacy selection screen 620. The list may be populated, for example, with pharmacies that the user has recently sent prescriptions to.

In an embodiment of the invention, the user may search for a pharmacy other than one listed, e.g., by entering in a text field part or all of the name, telephone number, address, postal or ZIP code, or other attribute of the desired pharmacy. In an embodiment of the invention, the application on the handheld device may transmit the search as a query, e.g., to a server, which may execute the search against one or more databases and then transmit the results to the handheld device, e.g., as a response to the query. Pharmacies that satisfy the query, if any, may be presented to the user, e.g., in a list (not pictured), and the user may select the desired pharmacy.

Figure 11:
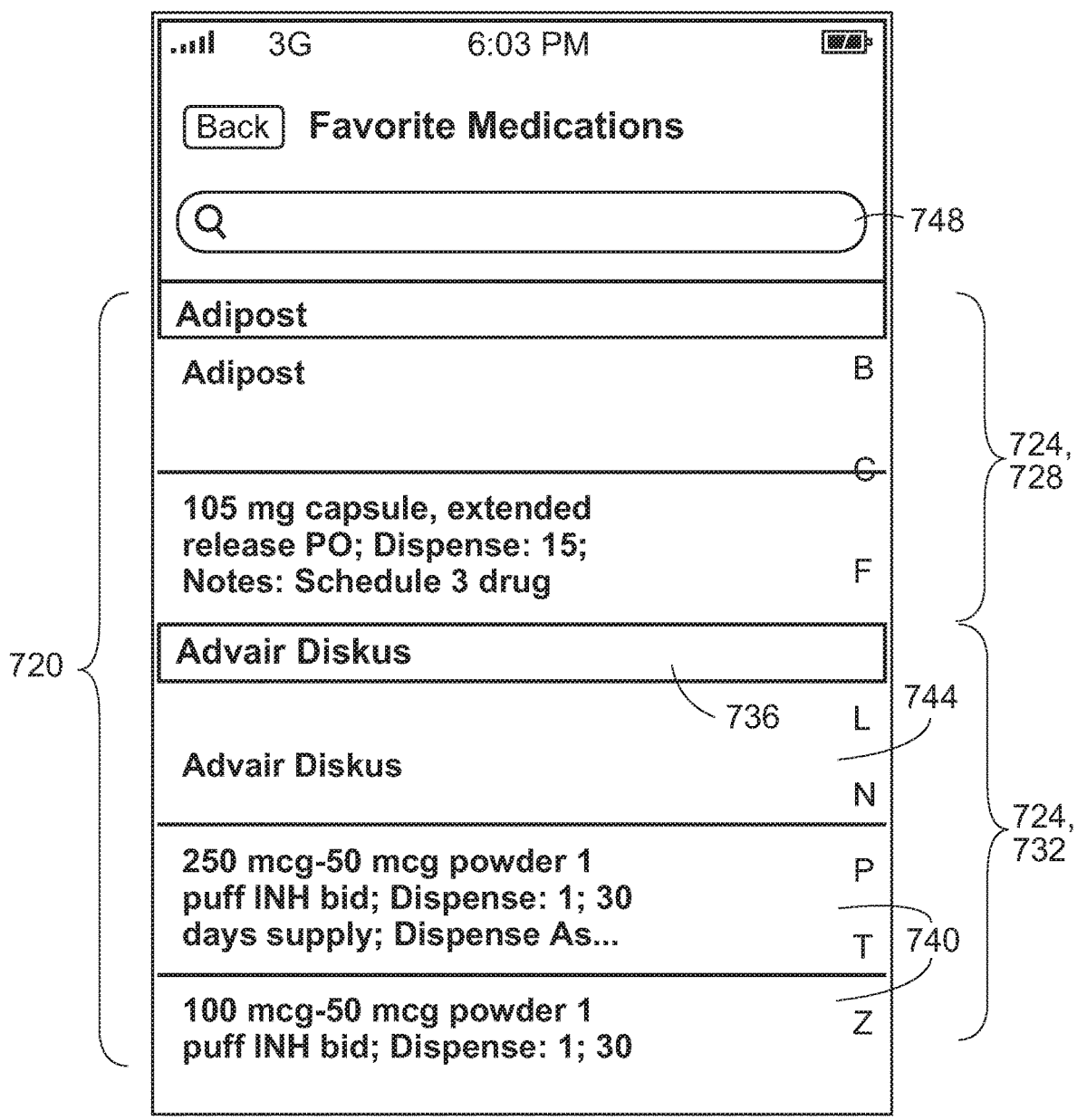
FIG. 11 depicts a medication selection screen that may be presented by an application on a handheld device in connection with an embodiment of the invention.

Returning to the flow of FIG. 4, the user may select a medication to prescribe in block 416. FIG. 11 displays a medication selection screen 700 that an application on a handheld device may display to a user in an embodiment of the invention. The depicted screen 700 displays a list 720 of entries 724 that correspond to drugs recently prescribed by the user. For example, the depicted screen 700 includes an entry 728 for Adipost and an entry 732 for Advair® Diskus®.

In an embodiment such as FIG. 11 depicts, an entry 732 for a drug may include a header 736 that begins the entry. The entry may include one or more items 740 that may represent prescriptions for the named drug with details such as dosage, form, amount, etc., already supplied. Each such item 740, for example, may correspond to the details of a prescription that the user has recently written.

An entry 732 may also include a blank item 744, which may, when selected in an embodiment of the invention represent mere selection of a drug to prescribe, leaving the other details of the prescription blank for the time being.

The medication selection screen 700 may include a text field, in an embodiment of the invention, in which the user may enter a partial or complete drug name and search for possibly matching drugs. As elsewhere, the search term may be transmitted, e.g., to a server, as a query, and the server may return, e.g., as a response to the query, a list of drugs, if any, that match the search term. The application may then present a list (not pictured) of matching drugs to the user, who may select the one intended for prescribing.

After selecting the medication, the user in an embodiment of the invention may supply and/or edit additional details of the prescription in block 418 of FIG. 4. For example, in an embodiment of the invention, additional details may include one or more of: the form of the drug; the route of administration; the amount of the dose; the frequency with which the drug is to be administered; the number of units to be dispensed; the number of days for which the patient is to take the drug; the number of refills, if any; whether the prescription is to be dispensed as written ("D.A.W."); any notes to be transmitted to the pharmacy; and any notes, e.g., for the patient's chart, that are not to be transmitted to the pharmacy.

If the user selected an item 740 such as in FIG. 11, in an embodiment of the invention, some or all items of additional information may receive values such as may have been provided, e.g., in the corresponding previous prescription. In that case, the user in block 418 of FIG. 4 may change or supplement the previously-supplied information. If the user selected only a drug in block 416 of FIG. 4, however, the user may then supply such additional information in the first instance in block 418.

Figure 12:
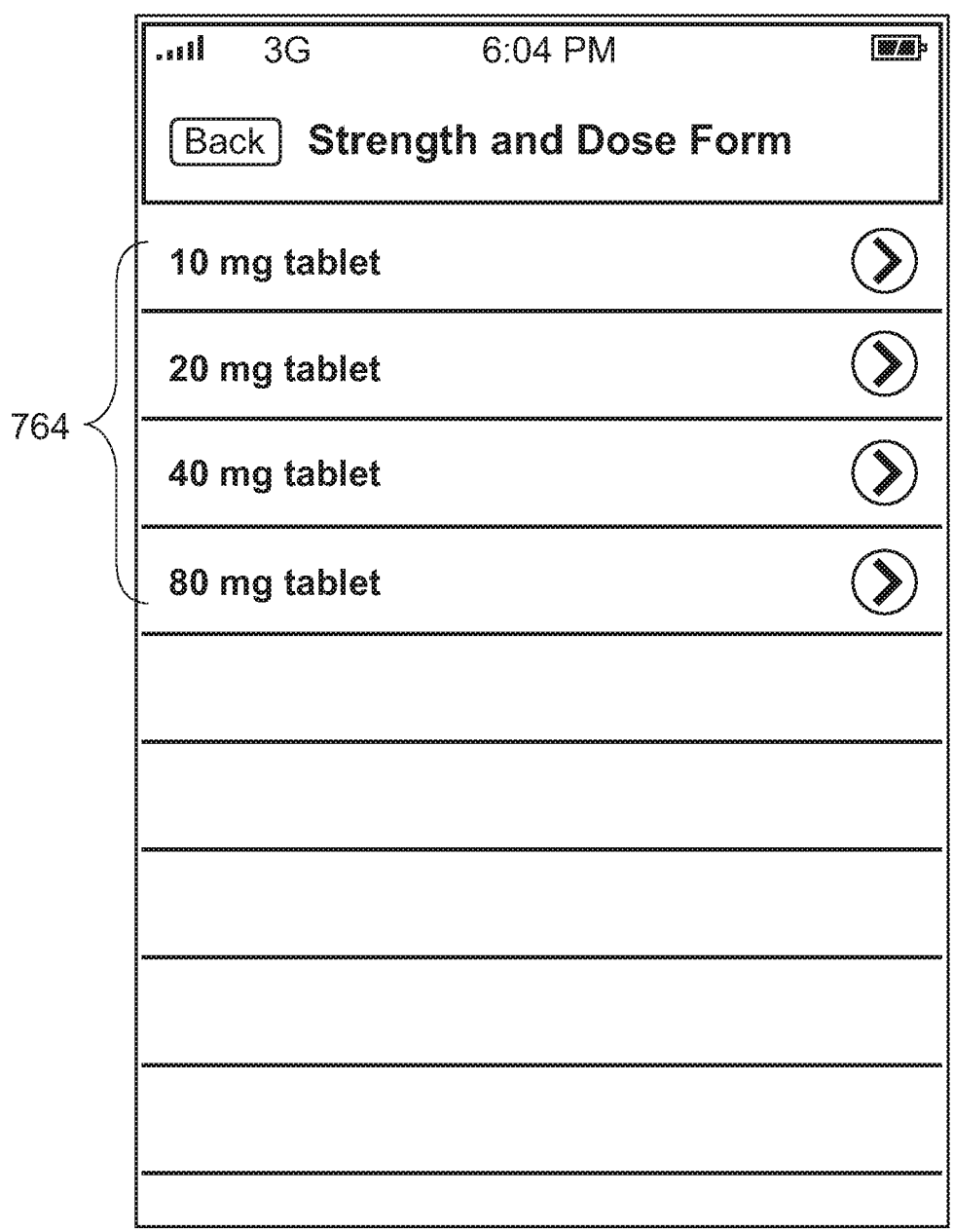
FIG. 12 depicts a strength and dose form selection screen that may be presented by an application on a handheld device in connection with an embodiment of the invention.

An application may provide appropriate user interface elements, e.g., such as are known in the art, for entry of additional information. For example, FIG. 12 depicts a strength and dose form selection screen 760 according to an embodiment of the invention. It will be appreciated that other user interface elements and/or arrangements may be used in an embodiment of the invention to obtain prescription information from a user.

In an embodiment of the invention, a user may save a prescription in progress or a completed prescription to a patient's chart, e.g., to be completed and/or transmitted later. In an embodiment of the invention, when the selected delivery option is "Sample", the electronic prescribing process may end with saving the completed prescription to the patient's chart.

In an embodiment of the invention, a user may be presented with other information related to the prescription, including for example, information related to the cost of the prescription and/or payment for it. For example, in an embodiment of the invention, formulary information may be presented (not pictured), e.g., regarding payment information provided by a prescription plan in which the patient participates. Formulary information may comprise identification of one or more drugs similar to the selected drug and/or approved for one or more of the same indications as the selected drug and payment information related to the identified drug or drugs. For example, if the relevant payer does not cover the selected drug (i.e., the drug is not on the formulary applicable to the patient), the information may identify one or more drugs that are on the formulary that may in some circumstances be prescribed instead of the selected drug. Formulary information may also comprise, e.g., limit or requirements imposed by the payer for the selected medication.

In an embodiment of the invention, information about drug pricing by the selected pharmacy may be available electronically, and in an embodiment of the invention, this pricing information (not pictured) may be presented to the user.

In block 420 of FIG. 4, the user may submit a prescription, e.g., for transmission to a printer, fax machine, and/or retail or mail-order pharmacy. In an embodiment of the invention, For example, in an embodiment such as FIGS. 9a and 9b depict, a "Send" button 606 may be provided that, when selected, causes the application on the handheld device to transmit one or more queries from the handheld device that include information making up the prescription and/or associated with it. As discussed below, the prescription may be processed by the server and then transmitted, e.g., for printing and/or electronic delivery. If processing is successful, the server may transmit, e.g., a response to the query or queries to the application on the handheld device, which may present, e.g., a confirmation message (not pictured).

If the "Auto-Print" delivery option was selected, in an embodiment of the invention, the confirmation message may indicate that a paper prescription has been printed at the selected printer. In block 422, the user may retrieve the printed prescription, sign it, and then deliver the signed prescription to the patient.

In embodiments of the invention, a prescription, once created, may be refilled and/or modified, e.g., from the patient's chart. A user may receive an alert (not pictured), generated, e.g., by an application on the handheld device according to an embodiment of the invention, when a prescription is to be renewed. Such an alert may be generated, e.g., automatically by the application or a server communicating with the application based on the record of the original prescription in the patient's chart. An alert may be generated in other ways, e.g., by a request from a pharmacy for authorization to renew or refill the prescription, or by a manual entry in an application on the handheld device, on another client-side device, and/or a server-side application, which may indicate, for example, that a renewal may be needed or requested.

In an embodiment of the invention, one or more of the servers discussed herein may be in some sense remote from one or more of the handheld device, printer server, and printer. "Remote" is used in the ordinary sense herein, and may indicate that one device is located in a facility that is commonly considered separate from the facility containing another device. For example, printers and print servers may commonly be configured to communicate only with devices connected to the same LAN and/or one or more physically proximate bridged networks, which may commonly span a single facility. A device such as a server may be considered remote, according to an ordinary use of the term, if, for example, it is located beyond the ordinary physical bounds of such networks.

A very large structure may be considered to comprise multiple facilities, and two devices may be considered remote despite being physically located within the same structure. For example, a medical center such as a hospital may comprise private practice groups in one part of a relatively large building or complex. A server, e.g., in a computer room, located in a part of the building apart from the space occupied by the practice groups such that an employee of the practice group would be unlikely to come near the server in the ordinary course of work in the practice group, may be remote from a device within the space occupied by the practice group.

Figure 13:
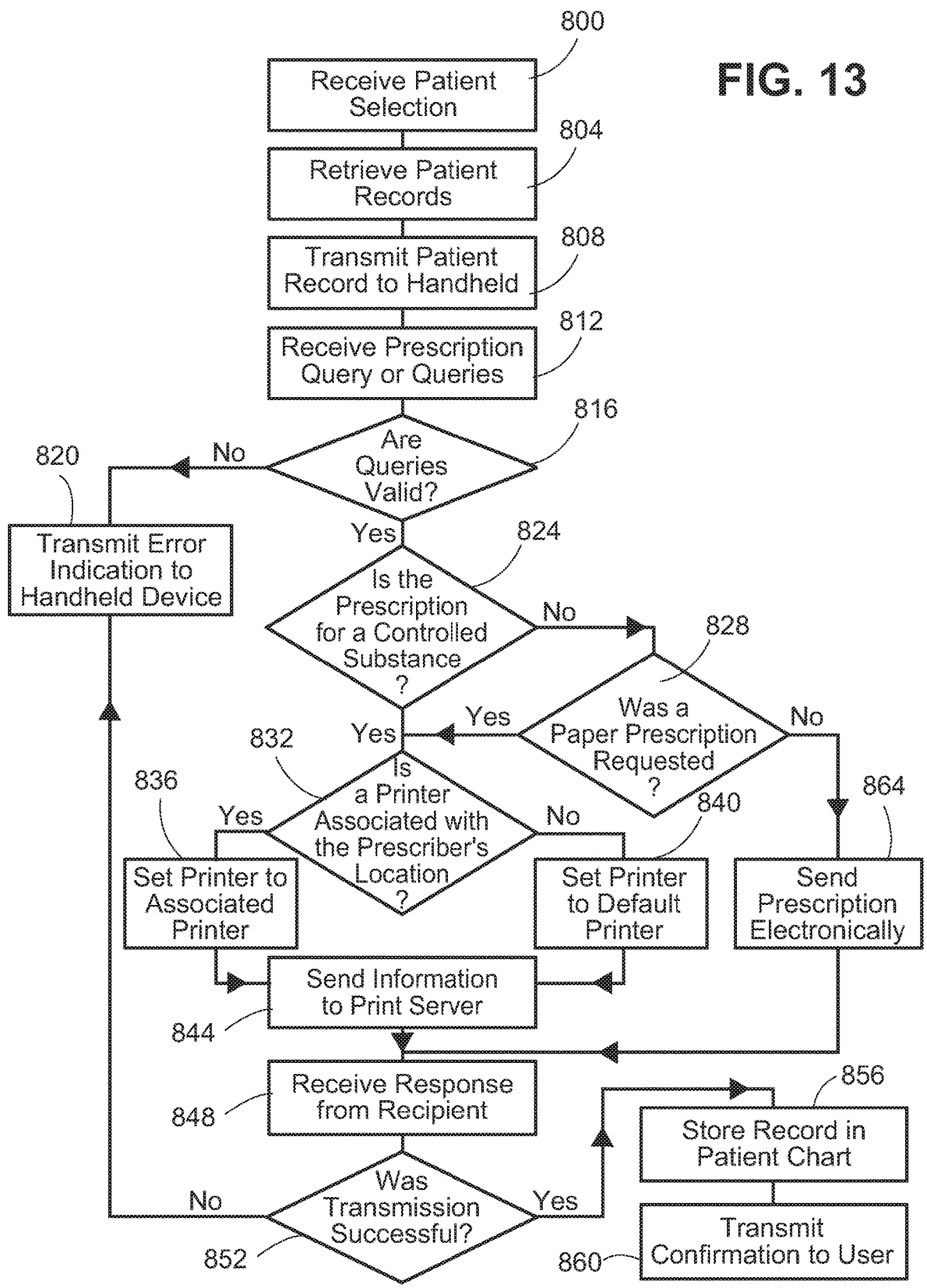
FIG. 13 depicts the flow of processing by a server in an embodiment of the invention.

FIG. 13 depicts processing. e.g., by one or more servers in communication with a handheld application according to an embodiment of the invention. The flow that FIG. 13 depicts may assume that the user of the handheld device has already created an account or is otherwise in a relationship with a service provider who operates the server. Some form of communications session may already have been established between the handheld application and a server, which may have involved, e.g., the user, device, and/or application providing identification and/or authentication to the server. It will also be appreciated that some or all communications to or from the handheld application may be secured, e.g., encrypted, by one or more methods while traversing all or part of the communication path.

In block 800, according to an embodiment of the invention, the server receives a request for information about a patient. In an embodiment of the invention, the request may include an identifier that uniquely identifies the patient. In response, the server may retrieve a patient's records (or cause them to be retrieved), e.g., from a database managed by a database management system, in block 804. Once retrieved, the responsive information may then be transmitted to the handheld application in block 808.

In block 812, the server or servers may receive information related to a prescription being generated, which may take the form of one or more queries. For example, a server may receive a request for drugs that match certain keywords or other search term, or a server may receive information otherwise related to a prescription. It will be appreciated that such queries may, in an embodiment of the invention, correspond or be related e.g., to, any or all of the information gathered by the handheld application in blocks 412-418 of FIG. 4. The server or servers may transmit requested or related information in response.

When the user submits the prescription in block 420 of FIG. 4, in an embodiment of the invention, the submission may take the form of one or more additional queries to the server in block 812.

In an embodiment of the invention, one or more of the queries may comprise information about the physical and/or logical location of the handheld device. For example, a device may include a GPS receiver and be able to transmit GPS coordinates. Instead of or in addition to the foregoing, a device may be able to determine its position, e.g., by triangulating based on the relative strengths of signals received from nearby cellular towers. Other location-based services include methods well known in the art, and a device in connection with an embodiment of the invention may use any technology and/or combination of technologies available to it to determine its physical location.

A device may also be considered to have a logical location based on its participation in one or more LANs. For example, a Wi-Fi™ network may use a SSID to identify itself. In an embodiment of the invention, a handheld device may transmit the SSID in one or more queries to indicate, e.g., to the server, which LAN the device is using. While identifying the LAN may not suffice to locate the handheld device precisely, this information may in an embodiment of the invention be used to identify resources (e.g., printers) that may be relatively near and/or accessible to the user of the device.

In block 816, the submitted information may be validated. The nature and scope of validation may vary. For example, in an embodiment of the invention, the server may check that the minimum information for a prescription has been provided and/or that all values are legitimate (e.g., that the specified pharmacy, drug, and/or form of administration exist). If information is missing, inconsistent, or otherwise invalid, an error message may be transmitted to the handheld application in block 820.

Validation in block 816 may go beyond that described above. In an embodiment of the invention, a server may make other checks. For example, the server may attempt to determine one or more of whether the prescribed dosage and/or frequency are consistent with therapeutic guidelines; whether the patient is taking one or more drugs that may interact adversely with the new prescription; and/or whether the patient's records show an allergy and/or other medical condition that may be inconsistent with the prescribed drug, among other possibilities. The server in an embodiment of the invention may retrieve a formulary associated with the patient, e.g., because the patient participates in a particular prescription plan, and determine whether the prescribed drug and/or drugs that may be substitutable for it are listed on the formulary. The results of such determinations may be transmitted to the handheld application, which may in an embodiment of the invention present information about one or more of the determinations to the physician. In response, the physician may, e.g., confirm or modify the prescription as entered and/or override prescription guidelines, among other possible responses.

If the submitted information is valid and/or otherwise acceptable, the server may then determine how to transmit the prescription for fulfillment. In some jurisdictions, for example, a prescription, e.g., for some controlled substances, may not be transmitted electronically. In an embodiment of the invention, as FIG. 13 depicts, a server may in block 824 determine whether a paper prescription with the physician's original signature may be required. If not, the server may then further determine in block 828 whether a printed prescription has been requested by the user.

If a prescription is to be printed, e.g., because it is required or requested, the server may in an embodiment of the invention determine where to transmit information to cause the prescription to be printed. If it is determined in block 832 that a particular printer has been specified, e.g., in one or more of the queries received in block 812, that printer may be selected. If no printer has been specified, then based, e.g., on location information that may have been received in block 812, the server may determine in block 832 whether a printer is associated with the reported location. The specified and/or associated printer may be selected in block 836.

If no associated and/or selected printer is identified, the server may in an embodiment of the invention select a default printer in block 840.

In block 844, a server may transmit information, e.g., to the printer and/or a print server associated with the printer. The information may include, e.g., identification and/or authorization information establishing that the server has sufficient privileges to use that printer, commands to manage the printer, print server, and/or printing queue associated with the printer and/or print server, and/or information and/or commands to direct the printer to print a prescription.

The nature of the transmitted information may vary in an embodiment of the invention. It will be appreciated that handheld devices and their operating systems may not include printer drivers, for example. In an embodiment of the invention, the server may have access to pattern information, e.g., in the form of one or more templates for one or more documents and/or types of documents, or other information and/or instructions that may be used to create a representation of a document. The server may use such pattern or other information to render the document into, e.g., a representation of the document in a page description language such as PostScript®, PCL, XPS (or OpenXPS), Portable Document Format (PDF), etc. The information transmitted in block 844 may in an embodiment of the invention be or comprise such a representation.

In block 848, the server may receive one or more responses from the printer and/or print server that received the printing job. The server may then in block 852 determine whether the response indicates successful printing of the prescription or, alternatively, it may determine that the response indicates that an error occurred. If an error is found, the server may in an embodiment of the invention transmit notification of the error to the handheld device, e.g., as in block 820.

In an embodiment of the invention, if the response indicates successful transmission and/or printing for the prescription, the server may then in block 856 update one or more records, e.g., in the database, which may include records representing the patient's chart. The server may also in block 860 transmit, e.g., a confirmation message to the handheld application, which may in turn display, e.g., a confirmation message to the user.

If a prescription is to be transmitted electronically, in an embodiment of the invention, the server in block 864 sends the prescription, e.g., by communicating with one or more computer systems associated with the pharmacy or mail order fulfillment center or by generating, e.g., an image of the prescription and transmitting it electronically to the destination. Upon successful transmission of the prescription, the server may in an embodiment of the invention transmit confirmation and/or take other actions, e.g., as described above.

It will be appreciated that there are several ways, including those well known in the art, to associate a printer with a physical and/or logical location. For example, administration in an embodiment of the invention may be accomplished, e.g., through a Web-browser based interface to one or more applications, e.g., using a Web server 344 (FIG. 3) and/or application server 348 (FIG. 3). For example, in an embodiment of the invention, one or more printers may be associated with one or more users and/or groups of users. Each respective printer may be associated with information that may include, e.g., the sizes and/or types of paper the printer is to be loaded with, one or more types of documents that are to be sent to the printer, and network information sufficient for the server to contact the printer.

In an embodiment of the invention, a computer system, which may be physically proximate to the printer, may serve as a print server. The computer system may be configured, e.g., to receive print jobs, to queue the received jobs, and/or to spool them to the printer. The print server may in connection with an embodiment of the invention register itself with a server as a possible destination for print jobs, e.g., using an application and/or daemon installed on the print server.

In an embodiment of the invention, the print server may initiate connection with a server that processes prescriptions, e.g., as described above. For example, one type of connection, in connection with an embodiment of the invention, may be a persistent HTTP (or HTTPS) connection, in which a print server may establish a connection by sending an HTTP request including, e.g., identification and/or authentication information, to the server. The print server may then periodically send a keepalive packet to the server to maintain the connection. If a connection times out despite the keepalive packets, the print server may reestablish the connection as required.

The server, for its part, may in an embodiment of the invention not respond to the HTTP request or requests until a document is to be sent to the print server. The response in such an embodiment may by information that the print server may use to cause the printer to print the document. The effect may be the same as if the server were to "push" the document to the print server or printer, even though the print server may in a sense "pull" the document from the server.

In an embodiment of the invention, the location of the printer, e.g., a street address, may be provided, e.g., through an administrative user interface such as described above. When a prescription or other document is to be printed, the street address may be used along with the location information provided by the device, e.g., to select the printer nearest to the user that is configured to accept that accept the kind of document for that user. Instead of or in addition to information about a printer's physical location, information that identifies one or more networks, e.g., SSIDs, may be associated with one or more printers. A server may then in an embodiment of the invention send, e.g., all print jobs originating from handheld devices that participate in a network with a particular SSID to the printer registered with that SSID.

Printing of more than one kind of document and/or other information may be supported in connection with an embodiment of the invention. An application according to an embodiment of the invention may present kinds of information and/or offer functions in addition to drug and prescription information and/or electronic prescribing. For example, the patient summary screen 480 that FIG. 7 depicts lists several results 508 of laboratory tests for the patient.

In an embodiment such as FIG. 7 depicts, a user may select a result, such as the result 512 of a lipid panel, and the result or results of the analysis may be presented, e.g., as a lab detail screen 900 such as FIG. 14 depicts. The lab detail screen may include results for one or more analytes 920. In an embodiment of the invention, one or more of the analytes 920 may be selectable, and selection of an analyte 920 may cause the application to present, e.g., more information (not pictured) about the test, analysis, and/or analyte.

The lab detail screen 900 may also include one or more buttons 924 and/or other items 928 that, when selected, cause display of a full report. In an embodiment of the invention, a "full report" may be a report that in one or more respects resembles a printed report, or an image of such report, that may include, e.g., all information such as may commonly be reported to the physician or other practitioner who requested the test. FIG. 15 depicts a display screen 950 that includes an example of a first page 960 of a report, in connection with an embodiment of the invention.

It will be appreciated, however, that inconveniences may attend use of a handheld device to review a full report such as FIG. 15 depicts in part. The iPhone® 3GS sold in 2009, for example, comprises a 480-by-320 pixel display that measures 3.5 inches diagonally. Such a display may not be the most convenient means for viewing a report that is formatted, e.g., for one or more standard US letter- or A4-sized pages.

Accordingly, in an embodiment of the invention, a full report display screen 950, such as FIG. 15 depicts, may include, e.g., a button or other control 964 that may be used to request printing of the full report. As FIG. 15 depicts, for example, a button 964 labeled "Auto Print" is provided. In an embodiment of the invention, selection of the button 964 may cause the handheld application to send one or more queries to a server requesting that a full report be printed. As discussed above in connection with printing a prescription, one or more of the queries may comprise information that, e.g., identifies and/or authenticates the user, device, and/or application, identifies one or more lab reports that are to be printed, and/or includes location information.

The server, receiving the query, may respond by, e.g., generating information that may cause a printer and/or print server to print the report, selecting a printer or print server to send the information to, and sending the information to the selected destination. As discussed above, one or more document types may be associated with a printer and/or location; accordingly, in an embodiment of the invention, the selection of the destination printer and/or print server may be based in part on the type of information and/or document.

Certain attributes that may be associated with one or more printers and/or print servers and/or used by a server to select a destination printer and/or print server are discussed above. Without limiting the foregoing discussion, attributes that may be considered in selecting a destination printer according to an embodiment of the invention may include, for example, the type of document (e.g., prescription, medical report, etc.), the paper size and/or type upon which the document is to be printed, the physical and/or logical location of the handheld device, the identity of the user and/or one or more groups and/or organizations with which the user may be affiliated, the identity of the patient and/or one or more groups and/or organizations with which the patient may be affiliated, one or more attributes of the information (e.g., partial vs. final report, normal vs. abnormal test result, controlled substance prescription, etc.), among many other possibilities.

In an embodiment of the invention, the location information and/or one or more specified attributes may determine the printer and/or print server to which the document is sent, and in an embodiment of the invention, such information may be used, e.g., to select one or more default and/or candidate printers and/or print servers, and the user may select, e.g., by using one or more display screens and/or user interface items (not pictured) presented by the handheld application to select a printer and/or print server. In an embodiment of the invention, the user may be able to select a printer and/or print server other than a default and/or candidate printer and/or print server selected, e.g., by the server.

The foregoing discussion primarily covers embodiments of the invention related to medical information and health care. But the discussion is intended to be illustrative and not limiting; the invention is of general applicability and limited only by the claims.

The invention claimed is:

1. A method for causing a selected printing system to print a document, the method being performed by a computer system participating in a data network comprising a plurality of handheld devices and a plurality of printing systems, and the method comprising:

receiving via the data network, from a handheld device of the plurality of handheld devices, transaction information that is related to a transaction and location information that specifies a first physical location, the first physical location being the physical location of the handheld device;

transmitting to the handheld device, via the data network, candidate information that is based on the location information and associated respectively with one or more of the plurality of printing systems;

receiving from the handheld device, via the data network, selection information based on the candidate information, the selection information specifying a second physical location;

approving the transaction based on the transaction information and the selection information;

selecting the selected printing system based on the selection information;

consequent to approving the transaction, transmitting to the selected printing system, via the data network, information to cause the selected printing system to print a document, the document being related to the transaction.

2. The method of claim 1, wherein the selected printing system is at a physical location remote from the computer system.

3. The method of claim 1, wherein the candidate information comprises default information associated respectively with a default one or more of the plurality of printing systems, the default one or more of the printing systems being designated before the receiving of the transaction information and before the receiving of the location information.

4. The method of claim 3, wherein the selected printing system is at a physical location remote from the computer system.

5. The method of claim 1, wherein the location information comprises GPS coordinates generated by the handheld device.

6. The method of claim 5, wherein the selected printing system is at a physical location remote from the computer system.

7. The method of claim 5, wherein the candidate information comprises default information associated respectively with a default one or more of the plurality of printing systems, the default one or more of the printing systems being designated before the receiving of the transaction information and before the receiving of the location information.

8. The method of claim 7, wherein the selected printing system is at a physical location remote from the computer system.

9. The method of claim 1, wherein the handheld device is at a physical location remote from the computer system.

10. The method of claim 9, wherein the selected printing system is at a physical location remote from the computer system.

11. The method of claim 9, wherein the candidate information comprises default information associated respectively with a default one or more of the plurality of printing systems, the default one or more of the printing systems being designated before the receiving of the transaction information and before the receiving of the location information.

12. The method of claim 11, wherein the selected printing system is at a physical location remote from the computer system.

13. The method of claim 9, wherein the location information comprises GPS coordinates generated by the handheld device.

14. The method of claim 13, wherein the selected printing system is at a physical location remote from the computer system.

15. The method of claim 13, wherein the candidate information comprises default information associated respectively with a default one or more of the plurality of printing systems, the default one or more of the printing systems being designated before the receiving of the transaction information and before the receiving of the location information.

16. The method of claim 15, wherein the selected printing system is at a physical location remote from the computer system.

17. A computer system for causing a selected printing system to print a document, comprising:
one or more programmable processors;
one or more computer-readable storage media operatively coupled to at least one of the processors; and
one or more network interfaces operatively coupled to at least one of the processors;
wherein the computer system is configured to participate, via one or more of the network interfaces, in a data network comprising a plurality of handheld devices and a plurality of printing systems; and
wherein at least one of the computer-readable storage media is encoded with instructions that, when executed by at least one of the programmable processors, cause the computer system at least to:
receive via the data network, from a handheld device of the plurality of handheld devices, transaction information that is related to a transaction and location information that specifies a first physical location, the first physical location being the physical location of the handheld device;
transmit to the handheld device, via the data network, candidate information that is based on the location information and associated respectively with one or more of the plurality of printing systems;
receive from the handheld device, via the data network, selection information based on the candidate information, the selection information specifying a second physical location;
approve the transaction based on the transaction information and the selection information;
select the selected printing system based on the selection information;
consequent to approving the transaction, transmit to the selected printing system, via the data network, information to cause the selected printing system to print a document, the document being related to the transaction.

18. The computer system of claim 17, wherein the location information comprises GPS coordinates generated by the handheld device.

19. The computer system of claim 17, wherein the candidate information comprises default information associated respectively with a default one or more of the plurality of printing systems, the default one or more of the printing systems being designated before the receiving of the transaction information and before the receiving of the location information.

20. The computer system of claim 19, wherein the location information comprises GPS coordinates generated by the handheld device.

21. A computer program product comprising one or more non-transitory computer-readable storage media encoded with instructions that, when executed by at least one processor within a computer system participating in a data network comprising a plurality of handheld devices and a plurality of printing systems, cause the computer system at least to:
receive via the data network, from a handheld device of the plurality of handheld devices, transaction information that is related to a transaction and location information that specifies a first physical location, the first physical location being the physical location of the handheld device;
transmit to the handheld device, via the data network, candidate information that is based on the location information and associated respectively with one or more of the plurality of printing systems;

receive from the handheld device, via the data network, selection information based on the candidate information, the selection information specifying a second physical location;

approve the transaction based on the transaction information and the selection information;

select the selected printing system based on the selection information;

consequent to approving the transaction, transmit to the selected printing system, via the data network, information to cause the selected printing system to print a document, the document being related to the transaction.

22. The computer program product of claim 21, wherein the location information comprises GPS coordinates generated by the handheld device.

23. The computer program product of claim 21, wherein the candidate information comprises default information associated respectively with a default one or more of the plurality of printing systems, the default one or more of the printing systems being designated before the receiving of the transaction information and before the receiving of the location information.

24. The computer program product of claim 23, wherein the location information comprises GPS coordinates generated by the handheld device.

* * * * *